United States Patent
Owoc (10) Patent No.: US 8,372,821 B2
(45) Date of Patent: Feb. 12, 2013

(54) STABLE AQUEOUS COMPOSITIONS COMPRISING BIOACTIVE CREATINE SPECIES

(76) Inventor: Jack H. Owoc, Davie, FL (US)

( * ) Notice: Subject to any disclaimer, the term of this patent is extended or adjusted under 35 U.S.C. 154(b) by 919 days.

(21) Appl. No.: 12/138,984

(22) Filed: Jun. 13, 2008

(65) Prior Publication Data

US 2009/0257997 A1    Oct. 15, 2009

Related U.S. Application Data

(60) Provisional application No. 61/043,619, filed on Apr. 9, 2008.

(51) Int. Cl.
*A01N 57/00* (2006.01)
*A61K 38/43* (2006.01)
*A61K 9/00* (2006.01)
*A61K 47/00* (2006.01)

(52) U.S. Cl. ........ 514/114; 424/94.1; 424/400; 424/439

(58) Field of Classification Search .................. 514/114; 424/94.1, 400, 439
See application file for complete search history.

(56) References Cited

U.S. PATENT DOCUMENTS

| 4,376,117 A | 3/1983 | Godfraind et al. |
| 5,973,005 A | 10/1999 | D'Amelio et al. |
| 2007/0015686 A1 * | 1/2007 | Heuer et al. ................. 514/2 |
| 2007/0037710 A9 * | 2/2007 | Gastner et al. ............... 504/343 |
| 2008/0058288 A1 | 3/2008 | Ramsbottom et al. |

FOREIGN PATENT DOCUMENTS

| GB | 1357813 A | 6/1974 |
| WO | WO 2006/034586 | 4/2006 |
| WO | WO 2008/025114 A1 | 3/2008 |
| WO | WO 2008/037047 * | 4/2008 |
| WO | WO 2009/079740 A1 * | 7/2009 |

OTHER PUBLICATIONS

Ferrini R et al, "Protective effect of creatinol O-phosophate (COP) on ventricular fibrillation and death induced by intravenous CaCl2 in mice", Arzneimittel Forschung, Drug Research, Ecv Editio Cantor Verlag, Aulendorf, DE, vol. 29, No. 9a, Jan. 1, 1979, pp. 1473-1474.

Nicaise J, "Creatinol O-phosophate (COP) and muscular performance; a controlled clinical trial", Current Therapeutic Research, Excerpta Medica, Trenton, NJ, US, vol. 17, No. 6, Jun. 1, 1975, pp. 531-534.

* cited by examiner

*Primary Examiner* — Ganapathirama Raghu
(74) *Attorney, Agent, or Firm* — Saliwanchik, LLoyd & Eisenschenk (57) ABSTRACT

Compositions containing one or more bioactive forms of creatine which are aqueous compositions in which the one or more bioactive forms of creatine do not appreciably degrade into creatinine. Also are methods for providing various beneficial effects which comprise administering aqueous compositions comprising at least one creating O-phosphate species to a mammalian subject, either chronically or acutely.

18 Claims, 1 Drawing Sheet

STABLE AQUEOUS COMPOSITIONS COMPRISING BIOACTIVE CREATINE SPECIES

CROSS-REFERENCE TO A RELATED APPLICATION

This application claims the benefit of U.S. provisional application Ser. No. 61/043,619, filed Apr. 9, 2008, which is hereby incorporated by reference in its entirety.

TECHNICAL FIELD

This disclosure relates generally to stable aqueous solutions of creatine, methods for their preparation and methods of use.

BACKGROUND OF THE INVENTION

Many nutritional supplements are available at various retail outlets, in many forms, including pills, powders, and liquids intended for human consumption.

One nutritional supplement that has become popular is creatine, whose IUPAC name is 2-(carbamimidoyl-methyl-amino)acetic acid, (CAS No. 57-00-1). Creatine occurs naturally in muscle and is believed to be an essential component in energy-producing metabolism and normal muscle function and growth. It is also believed by many to be useful to bodybuilders for increasing muscle mass, i.e., muscle-building.

Creatine is typically offered in powder, pill or capsule form. However, no aqueous-based formulations containing appreciable amounts of creatine, intended for oral human consumption, are readily available in the marketplace. This is because creatine is unstable in aqueous systems, in which it rearranges to creatinine. Creatinine is the breakdown product of creatine; creatinine has no effect on muscle protein.

BRIEF SUMMARY

The subject invention provides stable aqueous compositions of at least one biologically-active form of creatine. In a preferred embodiment, the compositions of the subject invention comprise:
a) at least one creatinol-O-phosphate (COP) species; and
b) water.

Advantageously, these compositions are stable across a wide range of pHs and temperatures. These formulations may have, for example, a pH of from about 3 to about 7 or more, and are stable at temperatures between 4° C. (or less) and 40° C. (or more). Advantageously, across this wide range of conditions, the concentration of bioactive species in these compositions does not decrease appreciably over periods of 40 or even 60 days or more.

The compositions of the subject invention may further comprise one or more additional materials selected from, for example, flavoring agents, colorants, viscosity modifiers, preservatives, fragrances, amino acids and their salts, vitamins, minerals, essential fatty acids, enzymes, co-enzymes, mono-glycerides, di-glycerides, tri-glyceride ester oils emulsifiers, hydrolyzed proteins, whey protein, stabilizers, flow modifiers, viscosity improvers, chelating agents, anti-oxidants, anti-microbials, benzoates, alcohols, esters of para-hydroxybenzoic acid, propionates, preservatives and surfactants.

The subject invention further provides methods for preparing and using these compositions.

The compositions of the subject invention can provide any one or more of wide range of physiological benefits including regeneration of ADP to ATP in muscle tissue, increasing the serum concentration of creatine, causing an increase in the skeletal muscle concentrations of creatine and phosphocreatine (PCr), increasing muscle fiber size/cross-sectional area and lean body mass, activating satellite cells, enhancing memory and cognitive function, enhancing the functional capacity of a mammal having a neuromuscular disease, increasing muscular strength, endurance and/or power, enhancing cognitive function in infants with inborn errors of creatine metabolism, and/or alleviating the deleterious effects of sleep deprivation.

BRIEF DESCRIPTION OF THE DRAWING

Result is given by milligram (mg) of creatinine present in ML (milliliters) of solution.

CM-325=Creatine Monohydrate at pH 3.0 and storage at 25° Celsius.

DCTP-3-25=Disodium Creatine Tetraphosphate at pH 3.0 and storage at 25° Celsius.

COP-3-25=Creatinol-O-Phosphate at pH 3.0 and storage at 25° Celsius.

CM-7-25=Creatine Monohydrate at pH 7.0 and storage at 25° Celsius.

DCTP-7-25=Disodium Creatine Tetraphosphate at pH 7.0 and storage at 25° Celsius.

COP-7-25=Creatinol-O-Phosphate at pH 7.0 and storage at 25° Celsius.

DETAILED DESCRIPTION

Figure 1:
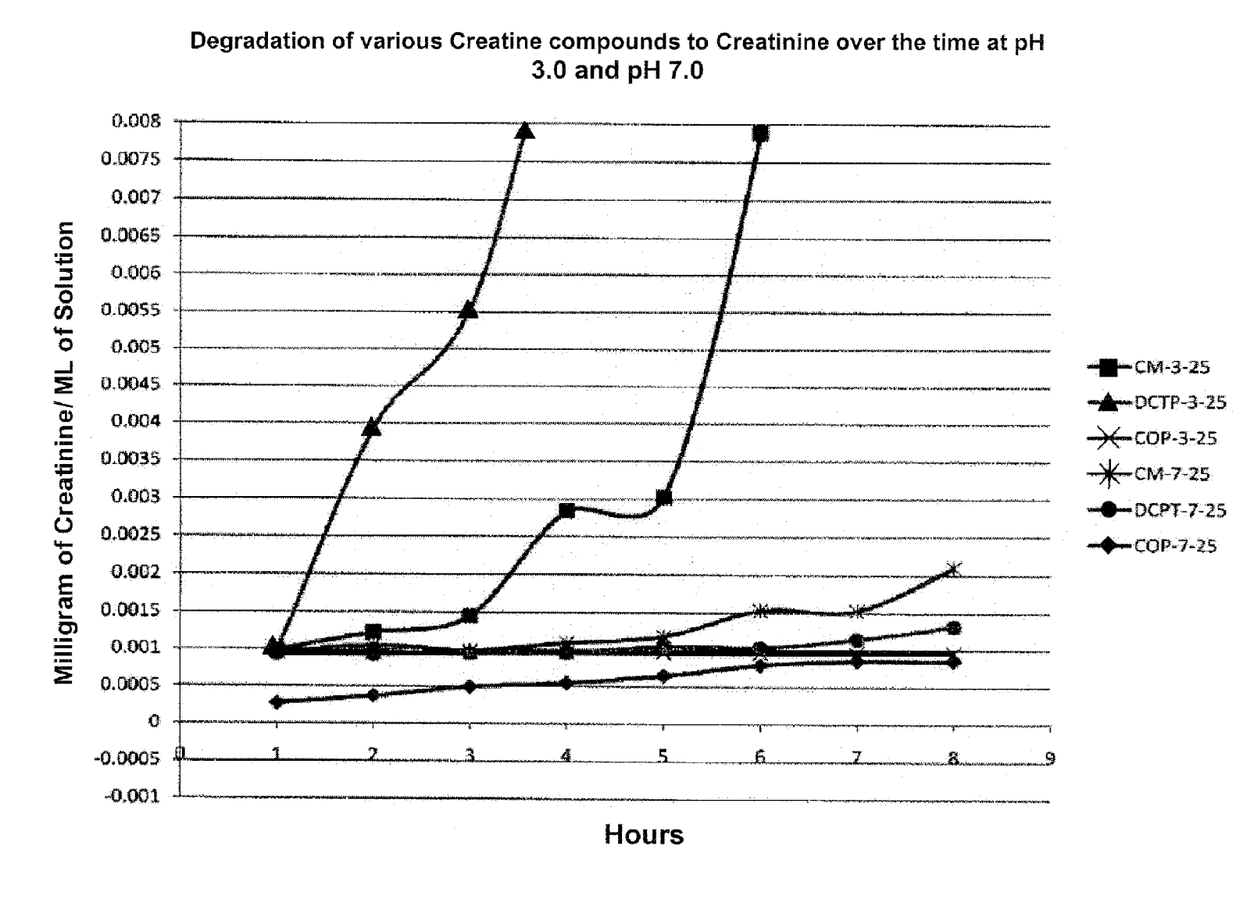
FIG. 1 is a graph that charts the increase in creatinine levels in solutions of various creatine salts over time. The solutions were prepared at pH 3 (Acid), and pH 7 (Neutral) conditions and were stored at room temperature (25° C.), and assayed by High Performance Liquid Chromatography immediately after preparation, and at several time intervals thereafter. These results indicate that while other creatine salts rapidly degrade, creationol-phosphate is stable and resistant to decomposition and even more stable at neutral pH condition.

The subject invention provides stable aqueous compositions of at least one biologically-active form of creatine. In a preferred embodiment, the compositions of the subject invention comprise:
a) at least one creatinol-O-phosphate (COP) species; and
b) water.

The subject invention further provides methods for preparing and using these compositions.

Specifically exemplified herein are compositions for oral use. The subject invention further provides compositions for injection as well as for topical administration.

In a specific embodiment, the subject invention provides aqueous compositions of matter suitable for oral administration to mammals including, without limitation, humans.

A composition as provided herein may be administered chronically. As used herein, "chronically" has its normal meaning, which generally means repeated ingestion over a period of several days, several weeks or even several months or more. Acute administration may also be utilized.

Specifically exemplified herein are compositions that comprise one or more forms of creatinol-O-phosphate (COP) (CAS No. 6903-79 3). Creatinol-O-phosphate is available in commercial quantities from Vital Pharmaceuticals, Inc., d/b/a VPX/Redline of Davie, Fla., among other sources. Creatinol-O-phosphate itself has the structure:

(I)

MW=197.13 and likely exists in a zwitterionic form to some extent. However, even in such zwitterionic form, one proton remains, which proton can be neutralized using any suitable basic substance including, without limitation, the oxides, hydroxides, caseinates, carboxylates, and carbonates of alkali metals and alkaline earth metals to afford aqueous solutions and/or suspensions of salts of creatinol-O-phosphate. Thus, when neutralized with an equimolar amount of a basic compound of a monovalent metal or an amine (including ammonia and alkyl-substituted amines), a material having the structure:

(II)

or a mixture comprising (II) and its zwitterionic form is provided, in which examples of M+ may include without limitation such cations as: sodium, lithium, potassium, rubidium, ammonium, any alkyl-substituted ammonium cation, and any other monovalent cation. When neutralized with an equimolar amount of a basic compound of a divalent metal or other cation, a material having the structure:

(III)

or a mixture comprising (III) and its zwitterionic form is provided, wherein n equals two, and in which examples of $M^{++}$ may include without limitation such cations as: zinc, calcium, and magnesium and any other di-positive cation. The materials described by formulae (I), (II), and (III) above, and the corresponding text in the description, including any and all of their zwitterionic forms, are all "creatinol-O-phosphate species" or "COP species". The distribution of concentration of the formulae shown above and the zwitterionic forms are pH dependent, as known to those skilled in the art.

A composition according to this disclosure may be caused to have any pH in the range of between about 1.5 and about 12.5 as desired, by adjusting such compositions using additions of appropriate amounts of strong or weak acids or bases including, without limitation, aqueous mineral acids including HCl, $H_3PO_4$, sodium hydroxide, etc. Preferably the pH is from about 3.0 to about 7.5.

To prepare a composition according to one embodiment of this invention, a desired amount of creatinol-O-phosphate (or any one or more creatinol-O-phosphate species) can be added to a selected volume of water, and sufficient stirring is effected to cause dissolution of the creatinol-O-phosphate (or any one or more creatinol-O-phosphate species) to afford an aqueous composition. Furthermore, according to one embodiment, the solution may be buffered before the addition of creatinol-O-phosphate or the solution may be may be made more acidic or alkaline prior to the addition of creatinol-O-phosphate.

According to one embodiment, the total concentration of creatinol-O-phosphate species in an aqueous solution provided hereby may be any amount between about 0.01% and about 20% (or more) by weight based on the total weight of the aqueous solution, including all percentages and ranges of percentages therebetween. According to another embodiment, the total concentration of creatinol-O-phosphate species in an aqueous solution provided hereby may be any amount between about 0.05% and about 7% by weight based on the total weight of the aqueous solution, including all percentages and ranges of percentages therebetween. According to another embodiment, the total concentration of creatinol-O-phosphate species in an aqueous solution provided hereby may be any amount between about 1% and about 5% by weight based on the total weight of the aqueous solution, including all percentages and ranges of percentages therebetween. In one embodiment, creatinol-O-phosphate (or any one or more creatinol-O-phosphate species) may be added to a natural beverage in any amount provided that an aqueous solution or suspension results.

According to another embodiment, one or more ions selected from the group consisting of: sodium, potassium, zinc, calcium, or magnesium (collectively, "metal cations") are caused to be additionally present in an aqueous solution comprising creatinol-O-phosphate wherein creatinol-O-phosphate is present in any amount as set forth above. These metal cations may be provided by adding a soluble salt or any other material containing any one or more of the metal cations to any aqueous solution containing one or more of a creatinol-O-phosphate species, or may be added to water or any aqueous solution prior to addition of one or more creatinol-O-phosphate species thereto.

The total concentration of these one or more metal cations in a composition according to this disclosure may be any amount between about 0.001% and about 20% by weight based on the total weight of the aqueous solution, including all percentages and ranges of percentages therebetween. Such metal ions may derive from a salt or compound containing a creatinol-O-phosphate species, or may derive from other ingredients added to the composition. Such other ingredients include, without limitation, alkali metal halides, alkaline earth metal halides, alkali metal carboxylates, alkaline earth metal carboxylates, and any other materials known to those skilled in the nutritional arts which comprise such metal cations as part of their molecular structure or formula, which are not deleterious to mammalian organisms at the concentration level at which they are present, which is generally known in the art.

In addition to ingredients containing one or more metal cations, a composition according to the subject invention may also include nutritional adjuvant materials including, for example, flavoring agents, colorants, viscosity modifiers, preservatives, fragrances, and other nutritional adjuvant materials. Other nutritional adjuvant materials include any substance that is generally recognized as promoting the health or function of a mammalian organism, including humans, or benefiting a composition useful therefor in terms of either its efficacy, appearance, stability, consistency, aroma, or viscosity. Such substances include amino acids and their salts, vitamins, minerals, essential fatty acids, enzymes, mono-glycerides, di-glycerides, tri-glyceride ester oils (including, for example vegetable oils and animal fats) emulsifiers, hydrolyzed proteins, whey protein, stabilizers, flow modifiers, viscosity improvers, chelating agents, enzymes, and surfactants, whether anionic, cationic or nonionic. The total amount of the one or more nutritional adjuvant materials above present in a composition according to this disclosure is present in any amount between about 0.01% and about 10% by weight based on the total weight of said composition, including all percentages and ranges of percentages therebetween.

In addition to ingredients containing one or more metal cations and other adjuvant materials, a composition according to this disclosure may also comprise one or more natural beverages. A natural beverage, as used herein, is a beverage suitable for human or animal consumption which contains the pulp, juice or any other constituent of a naturally-occurring fruit, vegetable, or animal product, whether from the wild, cultured, cultivated on a farm or otherwise domesticated. Natural beverages include without limitation materials such as milk products, soy products, ice cream, yogurt, citrus fruit juices, non-citrus fruit juices, and vegetable juices, or components of any of the foregoing, wherein said natural beverages are present in any effective amount to impart flavor to the compositions, which may be any amount between about 0.1% and about 99% by weight based on the total weight of said composition, including all percentages and ranges of percentages there between.

In addition to ingredients containing one or more metal cations and other adjuvant materials, a composition according to this disclosure may alternately comprise one or more synthetic beverages. A synthetic beverage is any beverage which is not a natural beverage.

In general, a composition according to this disclosure may be provided by combining and mixing the ingredients selected, including at least one creatinol O-phosphate species and any desired quantity of any one or more other ingredients specified herein. One advantage of compositions according to this disclosure is that they may be packaged at pH levels as low as about pH 3, in the cold or at about room temperature (22-25° C.) or only slightly elevated temperature (less than, for example, 30° C.), as opposed to many prior art compositions which typically require hot packaging methods that utilize specialized and expensive equipment and packaging materials.

Thus, it is evident that a composition according to this disclosure may be made quite palatable to mammals, including humans. Typical serving sizes may be any serving size in the range of about 1 milligram to about 50 grams, in an aqueous solution that is from about 20 ml to about 2500 ml in volume. The composition of COP species in an aqueous composition according to this disclosure is limited only by the solubility limit of the COP species and concentrations at or near the solubility limit are herein provided by contacting excess amounts of the COP or COP species in contact with water or an aqueous solution to provide a solution saturated with COP or a COP species. Such saturated solutions may then be diluted slightly, to afford a concentrate from which other COP species-containing compositions may be conveniently provided.

The compositions of the subject invention can be used in a variety of advantageous methods. For example, these compositions can be used in a method which the compositions of the subject invention may further comprise One or more additional materials selected from the group consisting of: flavoring agents, colorants, viscosity modifiers, preservatives, fragrances, amino acids and their salts, vitamins, minerals, essential fatty acids, enzymes, co-enzymes, mono-glycerides, di-glycerides, tri-glyceride ester oils emulsifiers, hydrolyzed proteins, whey protein, stabilizers, flow modifiers, viscosity improvers, chelating agents, anti-oxidants, anti-microbials, benzoates, alcohols, esters of para-hydroxybenzoic acid, propionates, preservatives and surfactants. Advantageously, these compositions are stable across a wide range of pHs and temperatures.

The compositions of the subject invention can be formulated for a variety of modes of administration. These formulations include, but are not limited to, compositions for oral administration, aqueous injectable formulations, injectable emulsion compositions, gel formulations, cream formulations, transdermal systems, transdermal patch systems, liquid buccal sublingual solutions, oral solid compositions, and oral liquid composition with protein.

The compositions of the subject invention can be used in a variety of advantageous methods. For example, these compositions can be used in methods which cause regeneration of ADP to ATP in muscle tissue, cause an increase in the serum concentration of creatine, cause an increase in the skeletal muscle concentrations of creatine and phosphocreatine (PCr), increase muscle fiber size/cross-sectional area and lean body mass, activate satellite cells, enhance memory and cognitive function, enhance the functional capacity of a mammal having a neuromuscular disease, increase muscular strength, endurance and/or power, enhance cognitive function in infants with inborn errors of creatine metabolism, or alleviate the deleterious effects of sleep deprivation.

Stability Study Materials and Methods

Creatinol-O-Phospate Solution: A batch of pure water or distilled water is put in a container, adjusted to a prescribed of pH 3 or pH 7 with a normal buffer and buffer salts, and heated to a temperature of 20° to 99° C. To 100 parts by weight of the warm water is added 0.1 to 0.3 parts by weight of the Creatinol-O-Phosphate (COP) which is dissolved by stirring. The pH is not particularly limited but is desirably not higher than pH 12 taking the physiological influences of the gastrointestinal tracts into consideration.

Creatine Monohydrate Solution: Similarly, a batch of pure water or distilled water is put in a container, adjusted to a prescribed of pH 3 or pH 7 with a normal buffer and buffer salts, and heated to a temperature of 20° to 99° C. To 100 parts by weight of the warm water is added 0.1 to 0.3 parts by weight of the Creatine Monohydrate (CM) which is dissolved by stirring.

Disodium Creatine Phosphate Tetrahydrate Solution: Similarly, a batch of pure water or distilled water is put in a container, adjusted to a prescribed or pH 3 or pH 7 with a normal buffer and buffer salts, and heated to a temperature of 20° to 99° C. To 100 parts by weight of the warm water is added 0.1 to 0.3 parts by weight of the Disodium Creatine Phosphate Tetrahydrate (DCPT) which is dissolved by stirring.

The aqueous solutions of COP, CM, and DCPT were prepared at pH 3 and pH 7 at a concentration of 0.250 mg/mL. They were stored at room temperature (25 C, 77 F), at refrigerator temperature (4 C, 39 F), and at elevated temperature (40 C, 104 F) in glass scintillation vials. These samples were assayed by HPLC at periodic intervals for 60 days and evaluated relative to Standard regression curves of known concentrations of the actives and of creatinine, the primary known degradation product of creatine. The results are presented below:

Stability Study Results
Preparation: Creatinol-O-Phosphate Aqueous Solution
Concentration: 0.250 mg/mL pH: 7.0 Condition: 40° C.

|                      |           |           | Time      |           |            |            |
|----------------------|-----------|-----------|-----------|-----------|------------|------------|
| Test                 | INITIAL   | 3 day     | 10 days   | 21 days   | 39 Days    | 60 days    |
| Creatinol-O-Phosphate | 0.226 mg/ml | 0.229 mg/ml | 0.238 mg/mL | 0.236 mg/mL | 0.258 mg/mL | 0.230 mg/mL |
| Creatinine           | 0.0 mg/mL | 0.0 mg/mL | 0.0 mg/mL | 0.0 mg/mL | 0.00 mg/mL | 0.00 mg/mL |
| pH                   | 7.0       |           |           |           | 5.5        | 5.5        | pH: 7.0 Condition: 25° C.

|                      |           |           | Time      |           |            |            |
|----------------------|-----------|-----------|-----------|-----------|------------|------------|
| Test                 | INITIAL   | 3 day     | 10 days   | 21 days   | 39 Days    | 60 days    |
| Creatinol-O-Phosphate | 0.226 mg/ml | 0.227 mg/ml | 0.236 mg/mL | 0.235 mg/ml | 0.239 mg/mL | 0.245 mg/mL |
| Creatinine           | 0.0 mg/mL | 0.0 mg/mL | 0.0 mg/mL | 0.0 mg/mL | 0.00 mg/mL | 0.00 mg/mL |
| pH                   | 7.0       |           |           |           | 5.3        | 5.3        | pH: 7.0 Condition: 4° C.

|                      |           |           | Time      |           |            |            |
|----------------------|-----------|-----------|-----------|-----------|------------|------------|
| Test                 | INITIAL   | 3 day     | 10 days   | 21 days   | 39 Days    | 60 days    |
| Creatinol-O-Phosphate | 0.226 mg/ml | 0.228 mg/ml | 0.237 mg/mL | 0.238 mg/mL | 0.244 mg/mL | 0.247 mg/mL |
| Creatinine           | 0.0 mg/mL | 0.0 mg/mL | 0.0 mg/mL | 0.0 mg/mL | 0.00 mg/mL | 0.00 mg/mL |
| pH                   | 7.0       |           |           |           | 5.2        | 5.2        |

Preparation: Creatinol-O-Phosphate Aqueous Solution  
Concentration: 0.250 mg/mL  
pH: 3.0 Condition: 40° C.

|                      |           |           | Time      |           |            |            |
|----------------------|-----------|-----------|-----------|-----------|------------|------------|
| Test                 | INITIAL   | 3 day     | 10 days   | 21 days   | 39 Days    | 60 days    |
| Creatinol-O-Phosphate | 0.247 mg/ml | 0.235 mg/ml | 0.239 mg/mL | 0.239 mg/mL | 0.241 mg/mL | 0.273 mg/mL |
| Creatinine           | 0.0 mg/mL | 0.0 mg/mL | 0.0 mg/mL | 0.0 mg/mL | 0.00 mg/mL | 0.00 mg/mL |
| pH                   | 3.0       |           |           |           | 3.0        | 3.0        | pH: 3.0 Condition: 25° C.

|                      |           |           | Time      |           |            |            |
|----------------------|-----------|-----------|-----------|-----------|------------|------------|
| Test                 | INITIAL   | 3 day     | 10 days   | 21 days   | 39 Days    | 60 days    |
| Creatinol-O-Phosphate | 0.247 mg/ml | 0.226 mg/ml | 0.237 mg/mL | 0.241 mg/ml | 0.247 mg/mL | 0.252 mg/mL |
| Creatinine           | 0.0 mg/mL | 0.0 mg/mL | 0.0 mg/mL | 0.0 mg/mL | 0.00 mg/mL | 0.00 mg/mL |
| pH                   | 3.0       |           |           |           | 3.1        | 3.1        | pH: 3.0 Condition: 4° C.

|  | Time | | | | | |
|---|---|---|---|---|---|---|
| Test | INITIAL | 3 day | 10 days | 21 days | 39 Days | 60 days |
| Creatinol-O-Phosphate | 0.247 mg/ml | 0.232 mg/ml | 0.243 mg/mL | 0.245 mg/ml | 0.249 mg/mL | 0.250 mg/mL |
| Creatinine | 0.0 mg/mL | 0.0 mg/mL | 0.0 mg/mL | 0.0 mg/mL | 0.00 mg/mL | 0.00 mg/mL |
| pH | 3.0 | | | | 3.1 | 3.1 |

The Creatinol-O-Phosphate (COP) aqueous solutions of the subject invention remains stable after 60 days of storage at 4° C., 25° C. and 40° C. at pH 3.0 and 7.0.

The data generated indicates that COP in aqueous solution is stable at room temperature for normal warehouse storage conditions, stable at 104° F. (40 C degrees) for shipping in hot weather trucks and/or overseas containers, and stable at 39° F. (4 C degrees) in coolers so that it can be stored under refrigeration conditions.

Preparation: Creatine Monohydrate Aqueous Solution
Concentration: 0.250 mg/mL
pH: 3.0 Condition: 25° C.

|  | Time | | | | | |
|---|---|---|---|---|---|---|
| Test | INITIAL | 3 day | 10 days | 21 days | 39 Days | 60 days |
| Creatine Monohydrate | 0.245 mg/mL | 0.219 mg/ml | 0.214 mg/mL | 0.151 mg/mL | 0.072 mg/mL | 0.037 mg/mL |
| Creatinine | 0.000 mg/mL | 0.026 mg/mL | 0.072 mg/ml | 0.111 mg/mL | 0.154 mg/mL | 0.167 mg/mL |
| pH | 3.0 | | | | 3.4 | 3.4 | pH: 7.0 Condition: 40° C.

|  | Time | | | |
|---|---|---|---|---|
| Test | INITIAL | 3 day | 39 Days | 60 days |
| Creatine Monohydrate | 0.257 mg/mL | 0.242 mg/ml | 0.251 mg/mL | 0.200 mg/mL |
| Creatinine | 0.000 mg/mL | 0.008 mg/mL | 0.068 mg/mL | 0.101 mg/mL |
| pH | 7.0 | | 7.4 | 7.4 |

Preparation: Creatine Monohydrate Aqueous Solution
Concentration: 0.250 mg/mL
pH: 3.0 Condition: 40° C.

|  | Time | | | | | |
|---|---|---|---|---|---|---|
| Test | INITIAL | 3 day | 10 days | 21 days | 39 Days | 60 days |
| Creatine Monohydrate | 0.245 mg/mL | 0.091 mg/ml | 0.036 mg/mL | 0.029 mg/mL | 0.030 mg/mL | 0.020 mg/mL |
| Creatinine | 0.000 mg/mL | 0.125 mg/Ml | 0.177 mg/ml | 0.186 mg/mL | 0.186 mg/mL | 0.187 mg/mL |
| pH | 3.0 | | | | 3.4 | 3.4 |

Creatine monohydrate in aqueous media show varying rates of decomposition to creatinine as well as other unknown compounds to an extent that 28% of creatine monohydrate converts to creatinine in 39 days at pH 7.0 and 74% is converted to creatinine at pH 3.0 when stored at 40° C. And 62% of creatine monohydrate is converted to creatinine at pH 3.0 when stored at 4° C.

Preparation: Disodium Creatine Phosphate Tetrahydrate Aqueous Solution
Concentration: 0.250 mg/mL
pH: 7.0 Condition: 40° C.

| Test | Time | | | | | |
|---|---|---|---|---|---|---|
| | INITIAL | 3 day | 10 days | 21 days | 39 Days | 60 days |
| Disodium Creatine Phosphate Tetrahydrate | 0.247 mg/mL | 0.166 mg/ml | 0.066 mg/mL | 0.015 mg/mL | 0.002 mg/mL | 0.00 mg/mL |
| Creatine Monohydrate | 0.00 mg/mL | 0.042 mg/mL | 0.114 mg/mL | 0.122 mg/mL | 0.108 mg/mL | 0.098 mg/mL |
| Creatinine | 0.000 mg/mL | 0.004 mg/mL | 0.012 mg/mL | 0.020 mg/ml | 0.030 mg/mL | 0.035 mg/mL |
| pH | 7.0 | | | | 7.8 | 7.8 | pH: 7.0 Condition: 25° C.

| Test | Time | | | | | |
|---|---|---|---|---|---|---|
| | INITIAL | 3 day | 10 days | 21 days | 39 Days | 60 days |
| Disodium Creatine Phosphate Tetrahydrate | 0.247 mg/mL | 0.229 mg/ml | 0.231 mg/mL | 0.182 mg/mL | 0.141 mg/mL | 0.140 mg/mL |
| Creatine Monohydrate | 0.00 mg/mL | 0.0.14 mg/mL | 0.041 mg/mL | 0.069 mg/mL | 0.089 mg/mL | 0.094 mg/mL |
| Creatinine | 0.000 mg/mL | 0.000 mg/mL | 0.000 mg/mL | 0.000 mg/ml | 0.000 mg/mL | 0.000 mg/mL |
| pH | 7.0 | | | | 7.8 | 7.8 |

It can be seen from the data above that DCPT solution at pH 7 converts to creatine monohydrate at 40 C and 25 C.

However, the newly formed creatine monohydrate (CM) starts to degrade to creatinine. This can be seen in the data at 40 C above where there is a gradual increase in the formation of CM up to the 21-day test to 0.188 mg/mL but then a decrease of CM at the 39-day test down to 0.108 mg/mL.

The mechanism for the conversion of DCPT to CM has not been elucidated but it is believed to be due to the hydrolysis of ester linkage of DCTP to yield free Creatine and inorganic phosphate.

Preparation: Disodium Creatine Phosphate Tetrahydrate Aqueous Solution
Concentration: 0.250 mg/mL
pH: 3.0 Condition: 40° C.

| Test | Time | | | | | |
|---|---|---|---|---|---|---|
| | INITIAL | 3 day | 10 days | 21 days | 39 Days | 60 days |
| Disodium Creatine Phosphate Tetrahydrate | 0.247 mg/mL | 0.000 mg/ml | 0.000 mg/mL | 0.000 mg/mL | 0.000 mg/mL | 0.00 mg/mL |
| Creatine Monohydrate | 0.004 mg/mL | 0.042 mg/mL | 0.017 mg/mL | 0.011 mg/mL | 0.012 mg/mL | 0.012 mg/mL |
| Creatinine | 0.000 mg/mL | 0.054 mg/mL | 0.086 mg/mL | 0.080 mg/ml | 0.081 mg/mL | 0.086 mg/mL |
| pH | 3.0 | | | | 3.4 | 3.4 | pH: 3.0 Condition: 25° C.

|  | Time | | | | | |
|---|---|---|---|---|---|---|
| Test | INITIAL | 3 day | 10 days | 21 days | 39 Days | 60 days |
| Disodium Creatine Phosphate Tetrahydrate | 0.247 mg/mL | 0.000 mg/ml | 0.000 mg/mL | 0.000 mg/mL | 0.00 mg/ml | 0.00 mg/mL |
| Creatine Monohydrate | 0.000 mg/ml | 0.095 mg/mL | 0.092 mg/mL | 0.065 mg/mL | 0.031 mg/mL | 0.013 mg/mL |
| Creatinine | 0.000 mg/mL | 0.014 mg/mL | 0.034 mg/mL | 0.050 mg/ml | 0.069 mg/mL | 0.075 mg/mL |
| pH | 3.0 | | | | 3.4 | 3.4 |

It can be seen from the data above that DCPT solution at pH 3 converts to creatine monohydrate at 40 C and 25 C.

However, the newly formed creatine monohydrate (CM) starts to degrade to creatinine. This can be seen in the data at 40 C and 25 C above where, in both cases, there is an increase in the formation of CM from the initial test to the 3-day test followed by a decrease of CM starting at the 10-day test.

Disodium Creatine Phosphate Tetrahydrate in aqueous media show varying rates of decomposition to creatinine as well as other unknown compounds. Disodium creatine phosphate tetrahydrate degrades rapidly (in less than 3 days) and converts to creatine monohydrate. The data showing this conversion is presented in the tables above. The newly formed creatine monohydrate then degrades to creatinine.

The mechanism for the conversion of disodium creatine phosphate tetrahydrate to creatine monohydrate has not been elucidated but it is believed to be due to the hydrolysis of ester linkage of disodium creatine phosphate tetrahydrate to yield free creatine and inorganic phosphate. The mechanism of hydrolysis may be affected by the ionization of the phosphate group (pKa1=2 and pKa2=6.2).

Following are examples which illustrate procedures for practicing the invention. These examples should not be construed as limiting. All percentages are by weight and all solvent mixture proportions are by volume unless otherwise noted.

EXAMPLE 1

Aqueous Injectable Formulations

One embodiment of the subject invention is an aqueous injectable composition. This composition is isotonic and sterile, and comprises Creatinol-O-Phosphate (COP). Preferably, the COP injectable preparation has a pH of about 3, and is substantially stable at room temperature for normal warehouse storage conditions, stable at 104° F. (40 C degrees) for shipping in hot weather trucks and/or overseas containers, and stable at 39° F. (4 C degrees) in coolers so that it can be stored under refrigeration conditions.

The composition can comprise a suitable aqueous solvent, and one or more preservatives, physical stabilizing ingredients and one or more buffers that can render the composition pH stable.

The composition may also contain nucleotides, oligonucleotides, monophosphates, diphosphates, triphosphates (and cyclic derivatives of these nucleotides), and amino acids, peptides, proteins and carbohydrates.

Specific Aqueous Injectable Formulations:

| Formulation I | |
|---|---|
| Ingredient | % w/v |
| COP | 2.10 |
| AMP | 12.5 |
| UTP | 0.10 |
| Amino Acids | 3.0-7.0 |
| Polysorbate 80 | 0.40 |
| Sodium CMC | 0.50 |
| Sodium Chloride | 0.90 |
| Benzyl alcohol | 0.90 |
| Buffer Salt(s) | QS to adjust to desired pH |
| Sodium Hydroxide | QS to adjust to desired pH |
| Water for Injection | QS to 100 |

| Formulation II | |
|---|---|
| Ingredient | % w/v |
| COP | 2.10 |
| AMP | 12.50 |
| UTP | 0.10 |
| Amino Acids | 3.0-7.0 |
| Polysorbate 80 | 0.40 |
| Sorbitol | 40.00 |
| Sodium Chloride | 0.90 |
| Benzyl alcohol | 0.90 |
| Buffer Salt(s) | QS to adjust to desired pH |
| Sodium Hydroxide | QS to adjust to desired pH |
| Water for Injection | QS to 100 |

| Formulation III | |
|---|---|
| Ingredient | % w/v |
| COP | 2.10 |
| Polysorbate 80 | 0.40 |
| AMP | 12.50 |
| UTP | 0.10 |
| Amino Acids | 3.0-7.0 |
| Sodium Citrate | 0.50 |
| Sodium Chloride | 0.90 |
| Benzyl alcohol | 0.90 |
| Buffer Salt(s) | QS to adjust to desired pH |
| Sodium Hydroxide | QS to adjust to desired pH |
| Water for Injection | QS to 100 |

EXAMPLE 2

Injectable Emulsion Composition

One embodiment of the subject invention is an injectable emulsion composition for human use. This composition is isotonic and sterile, and comprises Creatinol-O-Phosphate (COP). Preferably, the COP preparation has a pH of about 3, and is substantially stable at room temperature for normal warehouse storage conditions, stable at 104° F. (40 C degrees) for shipping in hot weather trucks and/or overseas containers, and stable at 39° F. (4 C degrees in coolers so that it can be stored under refrigeration conditions.

The composition can comprise a suitable aqueous solvent, a pharmaceutically acceptable oil (sesame, olive, castor, peanut, cotton seed, etc.), natural emulsifiers such as lecithin or any other synthetic emulsifier, be it of the polysorbate or ethoxylated glyceride type, one or more preservatives, physical stabilizing ingredients and one or more buffer salts that can render the composition pH stable.

The composition may also contain nucleotides, oligonucleotides, monophosphates, diphosphates, triphosphates (and cyclic derivatives of these nucleotides), and amino acids, peptides, proteins and carbohydrates.

Specific Injectable Emulsion Formulations:

| Formulation I | |
|---|---|
| Ingredient | % w/v |
| COP | 2.10 |
| AMP | 12.5 |
| UTP | 0.10 |
| Amino Acids | 3.0-7.0 |
| Sesame Oil | 2.0-12.0 |
| Polysorbate 80 | 0.40 |
| Sodium Chloride | 0.90 |
| Benzyl alcohol | 0.90 |
| Buffer Salt(s) | QS to adjust to desired pH |
| Sodium Hydroxide | QS to adjust to desired pH |
| Water for Injection | QS to 100 |

| Formulation II | |
|---|---|
| Ingredient | % w/v |
| COP | 2.10 |
| AMP | 12.50 |
| UTP | 0.10 |
| Amino Acids | 3.0-7.0 |
| Olive Oil | 1.0-15.0 |
| Lecithin | 0.50-5.0 |
| Sorbitol | 30.00 |
| Sodium Chloride | 0.90 |
| Benzyl alcohol | 0.90 |
| Buffer Salt(s) | QS to adjust to desired pH |
| Sodium Hydroxide | QS to adjust to desired pH |
| Water for Injection | QS to 100 |

| Formulation III | |
|---|---|
| Ingredient | % w/v |
| COP | 2.10 |
| Peanut Oil | 1.0-15.0 |
| Polysorbate 80 | 0.2-10.0 |
| AMP | 12.50 |
| UTP | 0.10 |
| Amino Acids | 3.0-7.0 |
| Sodium Citrate | 0.50 |
| Sodium Chloride | 0.90 |
| Benzyl alcohol | 0.90 |
| Buffer Salt(s) | QS to adjust to desired pH |
| Sodium Hydroxide | QS to adjust to desired pH |
| Water for Injection | QS to 100 |

EXAMPLE 3

Gel Formulation

One embodiment of the subject invention is a gel topical composition for skin application. This composition is clear or slightly opaque and has a gel consistency so that it can be spread on a skin surface. The composition comprises COP and has a pH of about 3 to 7. The composition is substantially stable at room temperature for normal warehouse storage conditions, stable at 104° F. (40 C degrees) for shipping in hot weather trucks and/or overseas containers, and stable at 39° F. (4 C degrees) in coolers so that it can be stored under refrigeration conditions.

The composition can comprise a suitable aqueous solvent, preservatives, polymers for imparting consistency, physical stabilizing ingredients and one or more buffers that can render the composition pH stable.

The composition may also contain nucleotides, oligonucleotides, monophosphates, diphosphates, triphosphates (and cyclic derivatives of these nucleotides), and amino acids, peptides, proteins and carbohydrates.

Specific Gel Formulations:

| Formulation I | |
|---|---|
| INGREDIENTS | % w/w |
| COP | 2.10 |
| Peptides/Polypeptides | 3.00 |
| AMP | 12.50 |
| UTP | 0.10 |
| Ubiquinone | 3.20 |
| Propylene Glycol | 12.0 |
| Carbomer | 1.00 |
| Buffer Salt(s) | QS to desired pH |
| Methylparaben | 0.20 |
| Propylparaben | 0.10 |
| Purified Water | QS to 100 |

| Formulation II | |
|---|---|
| INGREDIENTS | % w/w |
| COP | 2.10 |
| Peptides/Polypepetides | 3.00 |
| AMP | 12.50 |
| UTP | 0.10 |
| Ubiquinone | 3.20 |
| Glycerin | 5.00 |

Formulation II

| INGREDIENTS | % w/w |
|---|---|
| Hydroxyethylcellulose | 2.00 |
| Trietanolamine | QS to desired pH |
| Methylparaben | 0.20 |
| Propylparaben | 0.10 |
| Purified Water | QS to 100 |

Formulation III

| INGREDIENTS | % w/w |
|---|---|
| COP | 2.10 |
| Peptides/Polypepetides | 3.00 |
| AMP | 12.50 |
| UTP | 0.10 |
| Ubiquinone | 3.20 |
| Glycerin | 15.0 |
| Poloxamers 407/188 | 10.00 |
| Triethanolamine | QS to desired pH |
| Methylparaben | 0.025 |
| Propylparaben | 0.015 |
| Purified Water | QS to 100 |

EXAMPLE 4

Cream Formulations

One embodiment of the subject invention is a cream topical composition for skin application. This composition is an emulsion system or an opacified gel system and has a cream consistency so that it can be spread on a skin surface. The composition comprises COP and has a pH of about 3 to 7. The composition is substantially stable at room temperature for normal warehouse storage conditions, stable at 104° F. (40 C degrees) for shipping in hot weather trucks and/or overseas containers, and stable at 39° F. (4 C degrees) in coolers so that it can be stored under refrigeration conditions.

The composition can comprise a suitable aqueous solvent, preservatives, physical stabilizing ingredients, surfactants, moisturizers, and one or more buffers salt that can render the composition pH stable.

The composition may also contain nucleotides, oligo-nucleotides, monophosphates, diphosphates, triphosphates (and cyclic derivatives of these nucleotides), and amino acids, peptides, proteins and carbohydrates.

Specific Cream Formulations:

Formulation I

| INGREDIENTS | % w/w |
|---|---|
| COP | 2.10 |
| White Petrolatum | 20.0 |
| Stearyl Alcohol | 20.0 |
| Propylene Glycol | 12.0 |
| Peptides/Polypeptides | 3.00 |
| AMP | 12.50 |
| UTP | 0.10 |
| Ubiquinone | 3.20 |
| Sodium lauryl Sulfate | 1.00 |
| Methylparaben | 0.20 |
| Propylparaben | 0.10 |
| Buffer Salt(s) | QS to adjust pH |
| Purified Water | QS to 100 |

Formulation II

| INGREDIENTS | % w/w |
|---|---|
| COP | 2.10 |
| Peptides/Polypeptides | 3.00 |
| AMP | 12.50 |
| UTP | 0.10 |
| Ubiquinone | 3.20 |
| Mineral Oil | 15.0 |
| Lanolin Alcohol | 10.0 |
| Cetyl Alcohol | 0.20 |
| Beeswax | 4.00 |
| Sorbitan Monoleate | 5.00 |
| Glycerin | 5.00 |
| Borax | 0.30 |
| Trietanolamine | 0.70 |
| Methylparaben | 0.20 |
| Propylparaben | 0.10 |
| Buffer Salt(s) | QS to adjust pH |
| Purified Water | QS to 100 |

Formulation III

| INGREDIENTS | % w/w |
|---|---|
| COP | 2.10 |
| Peptides/Polypeptides | 3.00 |
| AMP | 12.50 |
| UTP | 0.10 |
| Ubiquinone | 3.20 |
| Glyceryl Monostearate | 10.0 |
| Lanolin | 2.00 |
| Glycerin | 10.0 |
| Stearyl Pyridinium Chloride | 1.50 |
| Methylparaben | 0.025 |
| Propylparaben | 0.015 |
| Buffer Salt(s) | QS to adjust pH |
| Purified Water | QS to 100 |

EXAMPLE 5

Transdermal Systems

One embodiment of the subject invention is a deep-penetrating transdermal composition. This composition can be a solution, a gel-like or an emulsion-like system or an opacified gel-like system having a consistency so that it can be spread on skin surface. The composition comprises COP which is substantially stable at room temperature for normal warehouse storage conditions, stable at 104° F. (40 C degrees) for shipping in hot weather trucks and/or overseas containers, and stable at 39° F. (4 C degrees) in coolers so that it can be stored under refrigeration conditions.

The composition can comprise suitable aqueous solvents, non-aqueous solvents, one or more penetrating enhancers, preservatives, physical stabilizing ingredients, surfactants, moisturizers, and buffers that can render the composition pH stable.

The composition may also contain nucleotides, oligonucleotides, monophosphates, diphosphates, triphosphates (and cyclic derivatives of these nucleotides), and amino acids, peptides, proteins and carbohydrates.

Specific Transdermal Systems:

| System I | |
|---|---|
| INGREDIENTS | % w/w |
| COP | 2.10 |
| N-methylpyrrolidone | 15.0 |
| Peptides | 3.00 |
| AMP | 12.50 |
| UTP | 0.10 |
| Ubiquinone | 3.20 |
| Alcohol USP | 2.00 |
| Benzyl alcohol | 1.00 |
| Buffer Salt(s) | QS to adjust pH |
| Purified Water | QS to 100 |

| System II | |
|---|---|
| INGREDIENTS | % w/w |
| COP | 2.10 |
| Peptides | 3.00 |
| AMP | 12.50 |
| UTP | 0.10 |
| Ubiquinone | 3.20 |
| Ethoxydiglycol | 25.0 |
| Alcohol USP | 2.00 |
| PEG esters and monoglycerides | 15.0 |
| Benzyl alcohol | 1.00 |
| Buffer Salt(s) | QS to adjust pH |
| Purified Water | QS to 100 |

| System III | |
|---|---|
| INGREDIENTS | % w/w |
| COP | 2.10 |
| Peptides | 3.00 |
| AMP | 12.50 |
| UTP | 0.10 |
| Ubiquinone | 3.20 |
| Propylene Glycol | 25.0 |
| Alcohol USP | 4.00 |
| Polysorbate 80 | 10.0 |
| Benzyl alcohol | 1.00 |
| Buffer Salt(s) | QS to adjust pH |
| Purified Water | QS to 100 |

EXAMPLE 6

Transdermal Patch Systems

One embodiment of the subject invention is a transdermal patch delivery system. The system can comprise a liner, an adhesive, backing and an aqueous liquid reservoir composition. The aqueous liquid reservoir composition being a solution or a suspension comprising COP. The COP is substantially stable at room temperature for normal warehouse storage conditions, stable at 104° F. (40 C degrees) for shipping in hot weather trucks and/or overseas containers, and stable at 39° F. (4 C degrees) in coolers so that it can be stored under refrigeration conditions.

The composition can comprise a suitable aqueous solvent, non-aqueous solvent(s), one or more penetrating enhancers, preservatives, physical stabilizing ingredients, surfactants, buffer salts that can render the composition pH stable.

The composition may also contain nucleotides, oligonucleotides, monophosphates, diphosphates, triphosphates (and cyclic derivatives of these nucleotides), and amino acids, peptides, proteins and carbohydrates.

Specific Liquid Reservoir for Transdermal Patch:

| Formulation I | |
|---|---|
| INGREDIENTS | % w/w |
| COP | 5.00 |
| N-methylpyrrolidone | 10.0 |
| Peptides | 3.00 |
| AMP | 12.50 |
| UTP | 0.10 |
| Ubiquinone | 3.20 |
| Alcohol USP | 45.0 |
| Benzyl alcohol | 1.00 |
| Buffer Salt(s) | QS to adjust pH |
| Purified Water | QS to 100 |

| Formulation II | |
|---|---|
| INGREDIENTS | % w/w |
| COP | 5.00 |
| Peptides | 3.00 |
| AMP | 12.50 |
| UTP | 0.10 |
| Ubiquinone | 3.20 |
| Ethoxydiglycol | 20.0 |
| Alcohol USP | 50.0 |
| Benzyl alcohol | 1.00 |
| Buffer Salt(s) | QS to adjust pH |
| Purified Water | QS to 100 |

| Formulation III | |
|---|---|
| INGREDIENTS | % w/w |
| COP | 5.00 |
| Peptides | 3.00 |
| AMP | 12.50 |
| UTP | 0.10 |
| Ubiquinone | 3.20 |
| Propylene Glycol | 20.0 |
| Alcohol USP | 40.0 |
| Polysorbate 80 | 5.0 |
| Benzyl alcohol | 1.00 |
| Buffer Salt(s) | QS to adjust pH |
| Purified Water | QS to 100 |

EXAMPLE 7

Liquid Buccal Sublingual Solution

One embodiment of the subject invention is an oral liquid composition for buccal sublingual administration. The composition can comprise COP and have a pH of about 3 to 7. The composition is being substantially stable at room temperature for normal warehouse storage conditions, stable at 104° F. (40 C degrees) for shipping in hot weather trucks and/or overseas containers, and stable at 39° F. (4 C degrees) in coolers so that it can be stored under refrigeration conditions.

The composition can comprise a suitable aqueous solvent or vehicle, a non-aqueous vehicle, preservatives, physical stabilizing ingredients, surfactants, and buffer salts that can render the composition pH stable.

The composition may also contain nucleotides, oligonucleotides, the monophosphates, diphosphates, triphosphates (and cyclic derivatives of these nucleotides), amino acids, vitamins and vitamin-like isoprenoids, peptides and one or more additional components selected from lipids, starches, carbohydrates, polyols, minerals, electrolytes, amino trace elements, colorings, flavors, artificial sweeteners, and anti-oxidants.

Specific Liquid Buccal Sublingual Solutions:

Example I

| INGREDIENTS | % w/w |
| --- | --- |
| COP | 2.10 |
| N-methylpyrrolidone | 10.0 |
| Peptides | 3.00 |
| AMP | 12.50 |
| UTP | 0.10 |
| Ubiquinone | 3.20 |
| Alcohol USP | 45.0 |
| Benzyl alcohol | 1.00 |
| Buffer Salt(s) | QS to adjust pH |
| Purified Water | QS to 100 |

Example II

| INGREDIENTS | % w/w |
| --- | --- |
| COP | 2.10 |
| Peptides | 3.00 |
| AMP | 12.50 |
| UTP | 0.10 |
| Ubiquinone | 3.20 |
| Ethoxydiglycol | 20.0 |
| Alcohol USP | 50.0 |
| Benzyl alcohol | 1.00 |
| Buffer Salt(s) | QS to adjust pH |
| Purified Water | QS to 100 |

Example III

| INGREDIENTS | % w/w |
| --- | --- |
| COP | 2.10 |
| Peptides | 3.00 |
| AMP | 12.50 |
| UTP | 0.10 |
| Ubiquinone | 3.20 |
| Propylene Glycol | 20.0 |
| Alcohol USP | 40.0 |
| Polysorbate 80 | 5.0 |
| Benzyl alcohol | 1.00 |
| Buffer Salt(s) | QS to adjust pH |
| Purified Water | QS to 100 |

EXAMPLE 8

Oral Solid Compositions

One embodiment of the subject invention is an oral solid composition in the form of a capsule (e.g. LiCap®) with a liquid composition as fill material containing from about 1% to about 20% of water. The liquid fill material has a pH of about 3 to 7 and is substantially stable at room temperature for normal warehouse storage conditions, stable at 104° F. (40 C degrees) for shipping in hot weather trucks and/or overseas containers, and stable at 39° F. (4 C degrees) in coolers so that it can be stored under refrigeration conditions.

The composition can comprise a suitable lipophilic solvent or vehicle, a hydrophilic non-aqueous vehicle, from about 1% to about 20% of water, preservatives, physical stabilizing ingredients, surfactants, and buffer salts that can render the composition pH stable.

The composition may also contain nucleotides, oligonucleotides, the monophosphates, diphosphates, triphosphates (and cyclic derivatives of these nucleotides), amino acids, vitamins and vitamin-like isoprenoids, peptides and one or more additional components selected from lipids, medium and short chain triglycerides, starches, polyols, carbohydrates, minerals, electrolytes, amino trace elements, colorings, and anti-oxidants.

Specific Fill Material Composition for Capsule:

Example I

| INGREDIENTS | % w/w |
| --- | --- |
| COP | 2.10 |
| Medium chain triglyceride | 15.0 |
| Peptides | 3.00 |
| AMP | 12.50 |
| UTP | 0.10 |
| Ubiquinone | 3.30 |
| Oleic Acid | 52.0 |
| Benzyl alcohol | 1.00 |
| Purified Water | 1.0-10.0 |

Example II

| INGREDIENTS | % w/w |
| --- | --- |
| COP | 2.10 |
| Peptides | 3.00 |
| AMP | 12.50 |
| UTP | 0.10 |
| Ubiquinone | 3.30 |
| Polysorbate 80 | 25.0 |
| PEG-40 Hydrogenated Castor Oil | 38.00 |
| PEG esters and monoglycerides | 15.0 |
| Benzyl alcohol | 1.00 |
| Purified Water | QS to 100 |

Example III

| INGREDIENTS | % w/w |
| --- | --- |
| COP | 2.10 |
| Peptides | 3.00 |
| AMP | 12.50 |

-continued

| Example III | |
|---|---|
| INGREDIENTS | % w/w |
| UTP | 0.10 |
| Ubiquinone | 3.30 |
| PEG-400 | 45.0 |
| PEG esters and monoglycerides | 9.00 |
| Polysorbate 80 | 20.0 |
| Benzyl alcohol | 1.00 |
| Buffer Salt(s) | QS to adjust pH |
| Purified Water | QS to 100 |

EXAMPLE 9

Oral Liquid Composition with Protein

One embodiment of the subject invention is an oral liquid composition containing from 1 gram to 100 grams of protein and from 1 gram to 100 grams of carbohydrates per serving and further comprising COP. The COP is stable at room temperature for normal warehouse storage conditions, stable at 104° F. (40 C degrees) for shipping in hot weather trucks and/or overseas containers, and stable at 39° F. (4 C degrees) in coolers so that it can be stored under refrigeration conditions.

The composition can comprise acid stable protein isolates, or a combination or blend of protein isolates, concentrates and hydrolyzates, and caseins in micellar forms, a suitable aqueous solvent or vehicle, a non-aqueous vehicle, preservatives, physical stabilizing ingredients, surfactants, and buffer salts that can render the composition pH stable.

The composition may also contain nucleotides, oligonucleotides, the monophosphates, diphosphates, triphosphates (and cyclic derivatives of these nucleotides), amino acids, vitamins and vitamin-like isoprenoids, peptides and one or more additional components selected from lipids, starches, carbohydrates, polyols, minerals, electrolytes, amino trace elements, colorings, flavors, artificial sweeteners, and anti-oxidants.

| High pH RTD Protein Blend Formulations | | |
|---|---|---|
| Ingredient | % w/w | Per 16 oz Serving |
| COP | 1.00 | 2.10 |
| Whey Protein Isolate | 6.000 | 30.00 |
| Whey Protein Concentrate | 0.640 | 3.20 |
| Whey Hydrolysate | 0.320 | 1.60 |
| Micellar casein | 0.320 | 1.60 |
| Casein Protein Hydrolysate | 0.000 | 0.00 |
| Potassium Chloride | 0.076 | 0.38 |
| Ascorbic Acid | 0.012 | 0.06 |
| Vitamin E TPGS | 0.052 | 0.26 |
| Riboflavin 100 | 0.000 | 0.00000010 |
| Niacin | 0.000 | 0.0020 |
| Pyrodoxine HCl | 0.000 | 0.000007 |
| Calcium Panthothenate | 0.000 | 0.0011 |
| Magnesium Maleate | 0.020 | 0.1000 |
| d-ribose | 0.040 | 0.2000 |
| Centromix E | 0.600 | 3.00 |
| Saflower Oil | 1.200 | 6.00 |
| Sunflower Oil | 1.200 | 6.00 |
| Medium Chain Triglycerides | 0.800 | 4.00 |
| L-Glutamine | 0.025 | 0.13 |
| Glucose Polymers (Rice trin) | 0.800 | 4.00 |
| Waxy Maize Starch | 1.000 | 5.00 |
| High Amylose Starch (Amylose ADP11P) | 0.100 | 0.50 |
| Magnessium Citrate | 0.124 | 0.62 |

| High pH RTD Protein Blend Formulations | | |
|---|---|---|
| Ingredient | % w/w | Per 16 oz Serving |
| Microcrystalline Cellulose | 0.100 | 0.50 |
| Malic Acid | 0.140 | 0.70 |
| Citric acid | 0.566 | 2.83 |
| Sodium Citrate | 0.140 | 0.70 |
| Sucralose | 0.011 | 0.06 |
| Glycerine | 3.000 | 15.00 |
| Na 2 EDTA | 0.050 | 0.25 |
| Sodium Benzoate | 0.090 | 0.45 |
| Potassium Sorbate | 0.190 | 0.95 |
| Water | QS | QS |
| TOTAL | 100 | 500.0 |

| Low pH RTD Protein Formulations | | |
|---|---|---|
| Ingredient | Per 16 oz serving | % w/w |
| COP | 2.10 | 0.25 |
| Whey Protein Isolate Acid Stable | 44.44 | 9.26 |
| Sucralose | 0.12 | 0.025 |
| Na EDTA | 0.24 | 0.050 |
| Potassium Sorbate | 0.96 | 0.200 |
| Sodium Benzoate | 0.48 | 0.100 |
| Citric Acid to pH 3.0 | QS | QS |
| Malic Acid to pH 3.0 | QS | QS |
| Water | 433.8 | 90.37 |
| Total | 480 | 100 |

| Low pH RTD Protein Formulations | | |
|---|---|---|
| Ingredient | Per 16 oz serving | % w/w |
| COP | 2.10 | 0.25 |
| Whey Protein Isolate Acid Stable | 44.44 | 9.26 |
| Sucralose | 0.12 | 0.025 |
| Waxy Maize Starch | 4.80 | 1.00 |
| Glucose Polymers (Rice trin) | 0.96 | 0.20 |
| Na EDTA | 0.24 | 0.050 |
| Potassium Sorbate | 0.96 | 0.200 |
| Sodium Benzoate | 0.48 | 0.100 |
| Citric Acid to pH 3.0 | QS | QS |
| Malic Acid to pH 3.0 | QS | QS |
| Water | QS | QS |
| Total | 480 | 100 |

Although this invention has been described and disclosed in relation to certain preferred embodiments, obvious equivalent modifications and alterations thereof will become apparent to one of ordinary skill in this art upon reading and understanding this specification and the claims appended hereto. This includes subject matter defined by any combination of any one of the various claims appended hereto with any one or more of the remaining claims, including the incorporation of the features and/or limitations of any dependent claim, singly or in combination with features and/or limitations of any one or more of the other dependent claims, with features and/or limitations of any one or more of the independent claims, with the remaining dependent claims in their original text being read and applied to any independent claims so modified. This also includes combination of the features and/or limitations of one or more of the independent claims with features and/or limitations of another independent claims to arrive at a modified independent claim, with the remaining dependent claims in their original text being read and applied to any independent claim so modified. Accordingly, the present disclosure is intended to cover all such modifications and alterations and is not intended to be necessarily limited by any one or more particular strict interpretations of the claims which now follow.

What is claimed is:

1. A method for providing a biologically-active form of creatine to a mammal via administration of an aqueous liquid composition, wherein said aqueous composition is stored for a period of at least 21 days before administration, wherein said method comprises:
   a) storing an aqueous composition comprising at least one creatinol-O-phosphate species and water for a period of at least 21 days; and
   b) administering said aqueous composition to a mammal.

2. The method, according to claim 1, wherein said aqueous composition further comprises one or more ions selected from the group consisting of sodium, potassium, zinc, calcium, and magnesium.

3. The method, according to claim 1, wherein said aqueous composition further comprises one or more additional materials selected from the group consisting of: flavoring agents, colorants, viscosity modifiers, preservatives, fragrances, amino acids and their salts, vitamins, minerals, essential fatty acids, enzymes, co-enzymes, mono-glycerides, di-glycerides, tri-glyceride ester oils emulsifiers, hydrolyzed proteins, whey protein, stabilizers, flow modifiers, viscosity improvers, chelating agents, anti-oxidants, anti-microbials, benzoates, alcohols, esters of para-hydroxybenzoic acid, propionates, preservatives and surfactants.

4. The method, according to claim 1, wherein said aqueous composition further comprises one or more natural or synthetic beverages.

5. The method, according to claim 1, wherein said aqueous composition further comprises a preservative present in an effective amount to inhibit microbial growth.

6. The method, according to claim 1, wherein said aqueous composition comprises at least one anion having a structure selected from the group consisting of:

and (including zwitterionic forms thereof).

7. The method, according to claim 1, wherein said aqueous composition is in the form of a composition for oral administration, an aqueous injectable formulation, an injectable emulsion composition, a liquid buccal sublingual solution, or an oral liquid composition with protein.

8. The method, according to claim 1, wherein the administration of the aqueous composition produces, in the mammal, one or more therapeutic effects selected from the group consisting of:
   (a) enhancing regeneration of ADP to ATP in the muscle tissue;
   (b) increasing the serum concentration of creatine;
   (c) increasing the skeletal muscle concentrations of creatine and phosphocreatine (PCr);
   (d) increasing muscle fiber size/cross-sectional area and lean body mass;
   (e) activating satellite cells;
   (f) enhancing memory and cognitive function;
   (g) increasing muscular strength, endurance or power; and
   (i) alleviating deleterious effects of sleep deprivation.

9. The method, according to claim 1, which enhances the functional capacity of a mammal having a neuromuscular disease.

10. The method, according to claim 1, which enhances cognitive function in infants with inborn errors of creatine metabolism.

11. The method, according claim 1, which comprises chronic administration of the composition.

12. The method, according to claim 1, wherein said aqueous composition is stored for a period of at least 60 days.

13. The method, according to claim 1, wherein said aqueous composition is stored at a temperature between about 4° C. and about 40° C.

14. The method, according to claim 13, wherein said aqueous composition is stored at room temperature.

15. The method, according to claim 1, wherein said aqueous composition has a pH of about 3 to about 7.

16. The method, according to claim 15, wherein said aqueous composition has a pH of about 3.

17. The method, according to claim 1, wherein said aqueous composition comprises 18. The method, according to claim 1, wherein said aqueous composition is an oral formulation and is administered orally to the mammal.

* * * * *

UNITED STATES PATENT AND TRADEMARK OFFICE
CERTIFICATE OF CORRECTION

PATENT NO.       : 8,372,821 B2
APPLICATION NO.  : 12/138984
DATED            : February 12, 2013
INVENTOR(S)      : John H. Owoc It is certified that error appears in the above-identified patent and that said Letters Patent is hereby corrected as shown below:

On the Title Page, Item (57)

Abstract,
Line 2, "creatine which" should read --creatine, which--

Abstract,
Line 6, "one creating O-phosphate" should read --one creatinol O-phosphate--

Signed and Sealed this
Fourth Day of June, 2013

Teresa Stanek Rea
*Acting Director of the United States Patent and Trademark Office*